United States Patent [19]

Forster et al.

[11] Patent Number: 4,904,606

[45] Date of Patent: Feb. 27, 1990

[54] METHOD AND APPARATUS FOR REDUCTIVE DECOMPOSITION AND ANALYSIS OF A SAMPLE

[75] Inventors: Alan R. Forster; Gregory J. Kamla, both of Houston, Tex.

[73] Assignee: Shell Oil Company, Houston, Tex.

[21] Appl. No.: 253,550

[22] Filed: Sep. 28, 1988

Related U.S. Application Data

[63] Continuation of Ser. No. 19,997, Feb. 27, 1987, abandoned.

[51] Int. Cl.$^4$ .............................. G01N 25/48
[52] U.S. Cl. ..................... 436/177; 261/76; 261/78.2; 422/80; 422/94; 436/155; 436/181
[58] Field of Search ............... 436/113, 121, 124, 155, 436/181, 177; 422/94, 78, 80; 261/76, 78.2

[56] References Cited

U.S. PATENT DOCUMENTS

| | | | |
|---|---|---|---|
| 3,703,355 | 11/1972 | Takahashi et al. | 436/155 |
| 3,853,474 | 12/1974 | Austin | 422/94 X |
| 3,904,366 | 9/1975 | Grasenick et al. | |
| 3,904,368 | 9/1975 | Takeyama et al. | |
| 3,923,464 | 12/1975 | Sitek et al. | |
| 4,018,562 | 4/1977 | Parks et al. | |
| 4,160,802 | 7/1979 | White et al. | 422/68 |
| 4,161,281 | 7/1979 | Erb et al. | |
| 4,161,282 | 7/1979 | Erb et al. | |
| 4,205,550 | 6/1980 | Swanson | 73/1 G |
| 4,228,795 | 10/1980 | Babington | |
| 4,261,511 | 4/1981 | Erb et al. | |
| 4,282,183 | 8/1981 | Bredeweg | 422/78 |
| 4,351,801 | 9/1982 | Bartke | 422/78 |
| 4,352,779 | 10/1982 | Parks | 422/52 |
| 4,352,781 | 10/1982 | O'Brien | 422/78 |
| 4,367,042 | 1/1983 | Smith, Jr. et al. | 356/315 |
| 4,569,918 | 2/1986 | Moore et al. | 422/80 |
| 4,582,654 | 4/1986 | Karnicky et al. | 261/81 |
| 4,620,670 | 11/1986 | O'Hughes | |

OTHER PUBLICATIONS

"Venturi Jet (Atomizer)-Type Burner For Determining Sulfur in Light Petroleum Products", Brown, C. W., Analytical Chemistry, vol. 32, No. 3 (1960) pp. 442-443.
"Advances in Wickbold Combustion Technique", Kunkel, E., Mikrochimica Acta. [Wein] (1976) II, pp. 1-8.
"Determination of Nitrogen in Petroleum Fractions by Combustion With Chemiluminescent Detection of Nitric Oxide", Drushel, H. V., Analytical Chemistry, vol. 49, No. 7 (1977) pp. 932-939.
"Determination of Total Sulfur In Hydrocarbons by Oxidative Microcoulometry", Moore, R. T., Clinton, P. and Barger, V., Analytical Chemistry, vol. 52 (1980) pp. 760-765.
"Determination of Low Levels of Sulfur in Organics by Combustion Microcoulometry", White, D. C., Analytical Chemistry, vol. 49, No. 11 (1977) pp. 1615-1618.
"Probeneintragssytem Mit Probeoverbrennung Oder Probenvorvedampfung fur Die Direkte Festsoffanalyse und fur Die Losungsspektralanalyse," Berndt, H., Spectrochimica Acta., vol. 39B, Nos. 9-11 (1984) pp. 1121-1128.
"Direct Liquid Sample Introduction for Flow Injection Analysis and Liquid Chromatography with Inductively Coupled Argon Plasma Spectrometric Detection", Lawrence, K. E. (Rice, G. W., and Fassel, V. A., Analytical Chemistry, vol. 56, (1984) pp. 289-292.
"On the Determination of Oxygen in Organic Solvents Using Inductively Coupled Plasma", Hauser, P. C. and Blades, M. N., Applied Spectroscopy, vol. 39, No. 5 (1985) pp. 872-877.

*Primary Examiner*—Barry S. Richman
*Assistant Examiner*—Jill Johnston

[57] ABSTRACT

Methods and apparatus are provided for decomposing and analyzing a sample. The methods reduce a nebulized sample in a hydrogen-rich atmosphere; the analysis method then analyzes the reaction gases for preselected analyte(s). The decomposition apparatus employs a nebulizer operatively connected to a reduction tube; the analysis apparatus employs appropriate detector(s) to analyze the reduced gases from the reduction tube for preselected analyte(s).

10 Claims, 2 Drawing Sheets

FIG. 1

- SAMPLE/MATERIAL MIXTURE 30
- 11
- NEBULIZER 10
- H2 40
- 22
- REDUCTION TUBE 20
- AEROSOL 14
- SEPTUM 26
- 13
- INERT GAS 12
- INLET SLEEVE 21
- FURNACE 50

FIG. 4

- 101 — NEBULIZE SAMPLE
- 102 — REDUCE SAMPLE
- 103 — ANALYZE SAMPLE GASES FOR PRESELECTED ANALYTE(S)

METHOD AND APPARATUS FOR REDUCTIVE DECOMPOSITION AND ANALYSIS OF A SAMPLE

This is a continuation of application Ser. No. 019,997, filed Feb. 27, 1987, now abandoned.

CROSS-REFERENCE TO SIMULTANEOUSLY FILED RELATED APPLICATIONS

"Method and Apparatus for Oxidative Decomposition and Analysis of a Sample", A. R. Forster and G. J. Kamla, Ser. No. 07/253,549.

"Method and Apparatus for Analysis of a Sample for Nitrogen", A. R. Forster and G. J. Kamla, Ser. No. 07/249,256.

"Method and Apparatus for Analysis of a Sample for Sulfur", A. R. Forster and G. J. Kamla, Ser. No. 07/249,255.

BACKGROUND OF THE INVENTION

This invention relates to analysis of materials, and more particularly, relates to method and apparatus for the reductive decomposition and quantitative determination of constituents of a sample.

A common form of sample preparation for elemental analysis involves the pyrolysis and reduction of a sample followed by the use of the resulting gases from this sample for the detection of the desired constituent(s) or analyte(s). Examples of this include nitrogen, halogen and sulfur determination using microcoulometry, and sulfur determination by measurement of differential darkening of an absorber ribbon. There is a problem associated with the reduction process which can cause unreliable analytical results and this problem centers on the sample introduction step.

If the sample is introduced using a syringe needle the needle must be placed directly into or very close to the hot zone of the reduction furnace to ensure the sample is transferred into the pyrolysis zone and pyrolyzed and reduced therein. Unfortunately, heavy organic fractions or salts can remain within the needle and possibly clog it temporarily, or permanently. One approach taken to overcome this problem is to introduce the sample into the hot portion of the furnace using a small boat which has been loaded with the sample when the boat was positioned in a relatively cool portion of the furnace tube. In either case, however, the sample introduction and subsequent pyrolysis and reduction is a transient process. Therefore, the hydrogen concentration in the reduction tube changes over time during this process. This can be detrimental in cases where equilibria involving hydrogen are important to the instrumental stability, sensitivity, or detection limits.

Accordingly, there is a need for a sample introduction scheme to allow for longer integration times in the detection phase which would then improve detection limits and also allow for use as an on-line monitor in process control, or as a chromatographic detector.

These and other limitations and disadvantages of the prior art are overcome by the present invention, however, and improved methods and apparatus are provided for decomposition and analysis of samples.

SUMMARY OF THE INVENTION

In a preferred embodiment of the present invention, methods and apparatus are provided for the quantitative determination of preselected constituents of a sample. In the presently preferred method for the analysis of a sample, the sample is first prepared for analysis by mixing a preselected quantity of the sample with a preselected quantity of a preselected material; the preselected material may serve to dilute and dissolve the sample, although the sample itself may also serve as this material. When the sample serves as the material, the analysis may be conducted substantially continuously. This sample and/or material may then be nebulized; the sample and/or material are nebulized in a nebulizer zone where an inert gas, such as argon, is used to disperse the sample and/or material into fine droplets which forms an aerosol with the argon gas. The aerosol is then transported to a hydrogen-rich reduction zone where the nebulized sample and/or material is completely pyrolyzed, or decomposed and reduced. The decomposed reduced products of the sample and/or material are then transported to an appropriate detection zone. In the detection zone the decomposed constituents of the sample and/or material are analyzed for preselected constituent(s) or analyte(s). Other methods, employing the initial portions of the above steps, may also be used to decompose a sample.

The presently preferred apparatus of the present invention is a nebulizer device positioned to deliver a liquid sample and/or material into the hot region of a reduction tube. A continuous aerosol stream of an appropriate preselected material and/or sample is injected into the reduction tube through the nebulizer with an argon carrier gas; the carrier gas serves to convert the preselected material and/or sample in the nebulizer into an aerosol form which becomes fully vaporized before it enters the reaction region of the reduction tube, where it is completely pyrolyzed, or decomposed, and reduced. A small portion of sample may be substantially continuously injected, with or without the preselected material, into the nebulizer by an appropriate pump, thereby providing for a substantially continuous portion of the sample to be reduced in the reduction tube. The sample may be dissolved and/or diluted in the material, or for appropriate samples only the sample may be injected into the reduction tube, via the nebulizer. The reduction tube is supplied with hydrogen and may also contain an appropriate catalyst to ensure complete reduction of a preselected constituent in the sample. The reaction products from the reduction tube are exhausted through an appropriate discharge opening and may be optionally filtered prior to passage to an appropriate detector, such as, for example, but not limited to an $H_2S$ or $NH_3$ analyzer. The output of the detector(s) may in turn be connected to an appropriate recorder or controller. Other apparatus, similar to that noted above (less the dectectors), may be employed to decompose a sample.

It is an object of the present invention to provide apparatus and methods for reductive decomposition of a sample.

It is an object of the present invention to provide an apparatus for quantitative analysis of preselected constituents of a sample.

It is also an object of the present invention to provide a method for quantitative analysis of preselected constituents of a sample.

It is a specific object of the present invention to provide a method for analyzing a sample, comprising, nebulizing said sample, transporting said nebulized sample to a decomposition zone, decomposing said sample in a hydrogen-rich atmosphere of hydrogen and an inert gas at a temperature sufficient to ensure complete reduction of said sample, transporting said decomposed sample to a detection zone, and analyzing said decomposed sample for a preselected analyte.

These and other advantages and objects of the present invention will become apparent from the following detailed description wherein reference is made to the Figures in the accompanying drawings.

IN THE DRAWINGS

FIG. 1 is a simplified functional diagram depicting the general arrangement of a nebulizer and reduction tube for use in the apparatus or methods of the present invention.

FIG. 4 is a simplified flow chart of the basic steps of the preferred method of the present invention.

DETAILED DESCRIPTION OF THE INVENTION

Figure 3:
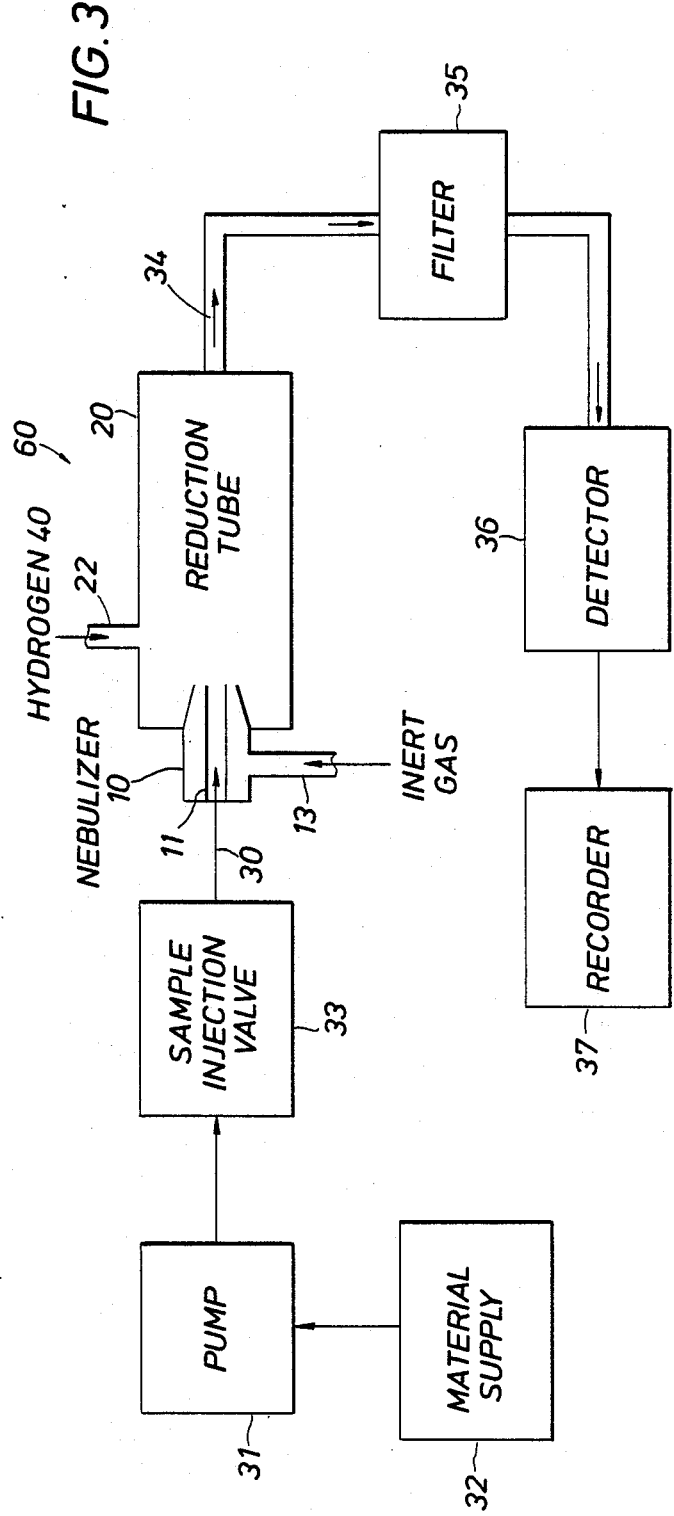
FIG. 3 is a simplified functional diagram of one embodiment of the apparatus of the present invention.

The present invention provides methods and apparatus for quantitative determinations of preselected constituents (or analytes) of a sample, and for decomposition of a sample. Referring now to FIG. 1, there may be seen a simplified functional diagram depicting the general arrangement of a nebulizer 10 and reduction tube 20 for use in the apparatus or methods of the present invention. More specifically, it may be seen that the present invention employs a nebulizer 10 operatively connected to the inlet sleeve 21 (or inlet neck) of a reduction tube 20. In particular, it may be seen that an appropriate liquid sample 30 may be injected into the nebulizer 10, via inlet 11, with or without a stream of preselected material, which may be a liquid solvent stream. A stream of inert gas 12, such as for example, but not limited to argon, is also supplied to the nebulizer 10, via inlet 13, to turn the sample and/or material 30 into an aerosol 14 which then is transported by the argon 12 into the reduction tube 20. The reduction tube 20 is supplied with hydrogen 40, via inlet 22, and may also contain an appropriate catalyst (not shown) and may be externally heated by furnace 50, to maintain an appropriate hot zone for complete reduction. The sample and/or material 30 are vaporized and pyrolyzed in the reduction tube 20 inlet zone. After pryolysis, the material and/or sample 30 reduces in the hydrogen 40 atmosphere. Under appropriate circumstances, as noted later herein, the sample may also be the preselected material. Appropriate catalyst (not shown) for a particular analyte, as noted later herein, may be included in the reduction tube 20 to ensure complete reduction of such a preselected analyte(s) of the pryolyzed sample in the reduction tube 20.

Since the nebulizer 10 is positioned in a relatively cool region at the front end of the reduction tube 20, the chances of the sample transport system becoming damaged or clogged, as in the prior art are eliminated. Thus, a sample introduction scheme, which may be substantially continuous, may be easily maintained.

The hydrogen supply 40 must be free of the constituents for which the sample is to be analyzed, or an appropriate adjustment to the data based upon the actual hydrogen supply employed must be determined before or after a sample is analyzed. The argon 12 flow rate must be sufficient to effectively nebulize the sample and/or material 30 and to transport the sample and/or material 30 to the hot zone and yet remain low enough so that it does not dilute the vaporized sample and/or material gases to point of inhibiting complete reduction of the sample. For high inert gas flow rates the inert gas may excessively dilute the sample and thus limit the ultimate sensitivity of the instrumental detection schemes that may be employed to analyze the reduction products. The sample and/or material 30 flow rate must be low enough so that complete reduction can occur without coke formation. Merely increasing the gas flows to compensate for excess sample and/or material input may not ensure complete reduction due to a decreased sample residence time within the reduction tube.

A pump, preferably with a precision flow output, such as for example, but not limited to an HPLC pump, is necessary for material and/or sample delivery to the nebulizer. A typical sample flow rate (depending upon the material type) is approximately 100 micro liters per minute ($\mu l/min$). Sample introduction may be achieved using an HPLC injection valve and sample loop, with the pump pushing the sample in the sample injection loop with an appropriate deaerated material from a material supply reservoir (see FIG. 3). Alternatively, the sample may be the material, or the sample may be dissolved or diluted in the material by mixing a preselected quantity of sample in a preselected quantity of material to provide a known concentration of sample.

The supply of hydrogen and argon into the reduction tube provides a positive pressure in the reduction tube, to exclude any undesirable gases. The discharge end of the reduction tube is also at a pressure slightly higher than atmospheric pressure. (See FIG. 2) This allows the reduced sample products to be positively swept from the reduction tube into subsequent sample discharge tubing. Thus, this configuration of nebulizer 10 and reduction tube 20 provide methods and apparatus for reductive sample decomposition. The sample discharge tubing may then be connected to appropriate detection or other apparatus.

Figure 2:
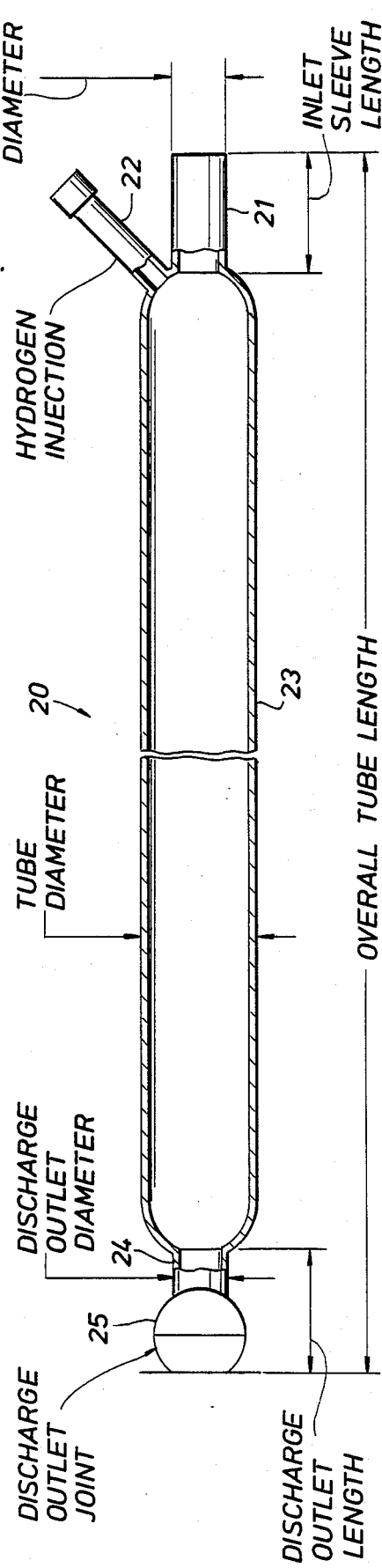
FIG. 2 is a simplified cross-sectional diagram depicting the arrangement of a reduction tube for use in the apparatus of the present invention.

Referring now to FIG. 2 there may be seen a simplified depiction of the arrangement of a reduction tube 20 for use in the apparatus of the present invention. More particularly, the reduction tube 20 is seen to consist of an outer envelope 23 of preferably quartz with an inlet connection 22 for injecting hydrogen into the tube, an inlet sleeve 21 (or inlet neck), and an outlet neck 24 and joint 25 at the opposite end for removal of any resulting gases. This outlet joint 25 is preferably a quartz to glass connection joint.

The inlet neck 21 of the reduction tube 20 allows for the introduction of a sample into the reduction tube/furnace. For the present invention an appropriate septum 26 and nebulizer 10 are inserted into the exterior opening of this inlet neck 21 (as shown functionally in FIG. 1).

The length of the reduction tube 20 is sized to allow for its use in an external furnace 50, such as for example, but not limited to a Dohrmann Model S-300 pyrolysis furnace; Dohrmann sells several commercial models of such furnaces. Once the length is thus roughly selected, the volume of the furnace tube is maximized to allow for larger sample and/or material injection rates while still achieving complete reduction of such materials and/or samples; this is generally accomplished by maximizing the outside diameter of the tube so that it narrowly fits inside the opening for a furnace tube in the external furnace 50.

The reduction hydrogen supply is preferably injected at the cool end of the tube, which is located physically outside the external furnace 50. This arrangement allows for a continuous, maximum outside diameter reduction tube of maximum volume to be contained in the external furnace 50. The reduction tube may optionally contain baffles, constrictive necks, and/or quartz chips to provide mixing of gases and vapors to ensure complete combustion; these baffles, etc., reduce the volume of the reduction tube while increasing its surface area. The reduction tube may also contain an appropriate catalyst.

For the Dohrmann Model S-300 pyrolysis furnace the furnace quartz reduction tube 20 has: an overall length of 575 mm, an outside diameter of 22 mm, a 6 mm outside diameter hydrogen injection line, a 12 mm outside diameter discharge outlet, a discharge outlet length of 25 mm, a 12 mm outside diameter inlet neck and an inlet neck length of 25 mm.

Referring now to FIG. 3, there may be seen a simplified functional diagram of one embodiment of the apparatus 60 of the present invention. More particularly, there may be seen a depiction of the nebulizer 10 and reduction tube 20, as previously shown and described for FIG. 1, as well as other items. There may be seen pump 31 (as described hereinbefore), interconnected with material supply 32, for delivering at a controlled rate, material to sample injection valve 33. The sample injection valve 33 may be operated to inject at least a portion of the sample (depending upon the length of the sample loop - not shown), at a controlled rate, into the nebulizer 10. For each such separate injection of sample, the sample stream replaces the material stream; accordingly, the sample must be introduced over a long enough time to ensure a steady-state reduction process, or the differences in chemical and reduction characteristics between the sample and material minimized, so that the sample portion does not significantly perturb the pyrolysis and reduction process. Alternatively, the sample may be dissolved and/or diluted in the material, and this mixture of sample and material injected, at a controlled rate, by the pump 31 into the nebulizer 10.

The nebulizer, as described hereinbefore, nebulizes the sample/ material stream which is then completely pyrolyzed and reduced in the reduction tube. The tube's discharge gases 34 may optionally be, and preferably are, filtered by filter 35, to remove any coke before passing the reaction gases into an appropriate detector 36. The detector 36 analyzes these gases 34 for a preselected constituent or analyte. Although only one detector 36 is depicted, more than one detector may be so employed to analyze these gases. The detector output may be recorded on an appropriate recorder 37 or used as an input for an appropriate controller (not shown). When more than one detector is employed, the flow rates may need to be increased to provide enough reduction gases for the number of detectors employed.

The sample and/or material may be totally sample, if the sample is a liquid at room temperature and capable of being nebulized. Any preselected material employed must dissolve the sample (solid or liquid), combust with no coke (if enough hydrogen is present), be liquid at room temperature and be extremely pure, i.e. and HPLC grade solvent. Examples of such materials are presently believed to be iso-octane and decalin. For aromatic samples/materials, the injection rates must usually be lowered to prevent coking of the reduction tube. The sample and/or material injection rates may be controlled by an appropriate liquid flow controller device (not shown).

The minimum inert gas flow rate is chiefly determined by the size of the nebulizer; this flow rate must be sufficient to ensure the nebulizer nebulizes the sample and/or material in an efficient and continuous manner. Higher inert gas rates tend to dilute the sample but may be acceptable from a detection limit point of view. The inert gas flow rate is controlled by an appropriate gas flow controller device (not shown).

The hydrogen flow rate into the reduction tube is as a minimum high enough to ensure complete reduction; although at very high rates, excessive sample dilution may occur. However, the flow rate must also be high enough to prevent coking. Further, as noted hereinbefore, the hydrogen supply is preferably free of the constituents for which the sample is to be analyzed. The hydrogen flow rate is controlled by an appropriate gas flow controller device (not shown).

As indicated hereinbefore the volume and length of the reduction tube is chiefly determined by the external furnace to be employed. The reduction tube may also contain an appropriate catalyst to ensure complete reduction of a preselected analyte. The nebulizer size is in turn chiefly determined by the physical dimensions of the reduction tube. That is, the nebulizer must be physically small enough to at least partially fit inside the inner diameter of the inlet neck (as depicted in FIG. 1).

As also noted hereinbefore, the flow rate of inert gas into the nebulizer is chiefly determined by the size and type of nebulizer. The minimum flow rate is that which still effectively nebulizes the sample and/or material and the maximum flow rate is determined by excessive dilution of the analyte.

As previously noted herein, the hydrogen flow rate must be sufficient to completely reduce the sample. Thus, the minimum hydrogen flow rate is determined by the sample injection rate, which is in turn related to the nebulizer size and type, and the inert gas flow rate. The hydrogen flow rate is at least equal to, but preferably greater than, the inert gas flow rate; as long as this flow rate is still a sufficient flow rate to provide enough hydrogen to completely reduce the sample.

The sample and/or material flow rate is thus chiefly determined by the nebulizer size and type, and the inert gas flow rate, i.e. these rates/sizes must be sufficient to efficiently nebulize the sample and/or material without any coking of the reduction tube.

Thus, it may be seen that the present invention also provides methods for decomposing and/or analyzing a sample for preselected analyte(s). FIG. 4 depicts the basic steps of the methods of the present invention. In particular, analysis method of the present invention nebulizes the sample 101, pyrolyzes and reduces this nebulized sample 102, and then analyzes the gases from the reduced sample for preselected analytes 103. However, the decomposition method nebulizes the sample 101 and then pyrolyzes and reduces this nebulized sample 102; thus, the decomposition method only employs the first two basic steps (blocks 101 and 102) depicted in FIG. 4.

When samples containing nitrogen compounds are pyrolyzed and reduced with hydrogen, the nitrogen is converted to ammonia. A nickel catalyst at about 800° C., may be used in the reduction tube to ensure complete reduction occurs. The ammonia in the reaction gases may be detected using microcoulometry, fluorescence, and/or mass spectrometry.

When samples containing sulfur compounds are pyrolyzed and reduced with hydrogen, the sulfur is converted to hydrogen sulfide. A platinum catalyst at about 1150° C., may be used in the reduction tube to aid in the reduction process and ensure complete reduction. The hydrogen sulfide in the reaction gases may be detected using the differential darkening of lead acetate-impregnated tape, microcoulometry, fluorescence, and/or mass spectrometry. The presently preferred detection technique is to direct the gases towards a moistened ribbon or tape impregnated with lead acetate, where the sulfide reacts with the lead to form lead sulfide which is black; the rate of blackening of the moving tape is directly proportional to the sulfide content of the reaction gases.

When samples containing halogen compounds are pyrolyzed and reduced with hydrogen, the halogens are reduced to their appropriate acid halide. These halides may be detected by conductivity, microcoulometry, (excluding fluorine), and/or gravimetry (excluding fluorine).

When samples containing carbon compounds are pyrolyzed and reduced with hydrogen, the carbon is converted into methane. The methane may be detected using a flame ionization detector and/or a mass spectrometer.

When samples containing oxygen compounds are pyrolyzed and reduced with hydrogen, the oxygen is reduced to water. The water may be detected using microcoulometry, Karl Fischer titration, gravimetry, and/or ultra-violet laser-excited fluorescence. Karl Fischer titration for water employs a typical stabilized Karl Fischer reagent which consists of iodine and sulfur dioxide in pyridine and methyl cellusolve. The reaction between water and the components within the Karl Fischer reagent reduce the iodine and this reduction of iodine is measured amperometrically.

In microcoulometry, a titration cell is maintained at a constant concentration of titrant ion through coulometric generation. Addition of the analyte species of interest depletes the concentration of the titrant ion. The current necessary to coulometrically maintain the titrant ion concentration is a measure of the amount of analyte species present. In mass spectrometry, the reduction gases are ionized, the ions are separated as a function of mass, and the ions of a predetermined mass or mass range are then detected. In gravimetry, the analyte of interest is chemically complexed to a substrate and the change in weight of the substrate is directly proportional to the analyte present. However, some consideration must be made, for the analytes sought to be detected and the types of samples to be analyzed, to prevent analyte interferences in a given detection technique that is capable of detecting more than one analyte sought to be detected.

Many other variations and modifications may be made in the apparatus and techniques hereinbefore described, by those having experience in this technology without departing from the concepts of the present invention. Accordingly, it should be clearly understood that the apparatus and methods depicted in the accompanying drawings and referred to in the foregoing description, are illustrative only and are not intended as limitations on the scope of the invention.

What is claimed is:

1. A method for analyzing a sample, comprising:
   nebulizing at least a portion of said sample,
   transporting said nebulized sample to a decomposition zone,
   decomposing said sample in a hydrogen-rich atmosphere of hydrogen and an inert gas at a temperature sufficient to ensure complete reduction of said sample.
   transporting said decomposed sample to a detection zone, and
   analyzing said decomposed sample for a preselected analyte.

2. A method as described in claim 1, wherein said nebulizing of said sample comprises,
   injecting a portion of said sample at a preselected rate into a nebulizing zone, and
   injecting an inert gas into said nebulizing zone at a preselected rate to form an aerosol with said injected sample.

3. Apparatus for analyzing a sample, comprising:

means including an inert gas for nebulizing at least a portion of such sample to form an aerosol containing said portion of said sample and inert gas, means for transporting said aerosol to a decomposition zone, means for decomposing said aerosol in a hydrogen-rich atmosphere of hydrogen and said inert gas at a temperature sufficient to ensure complete reduction of said portion of said sample in said aerosol in said decomposition zone, means for transporting said portion of said sample from said decomposition zone to a detection zone, and means for analyzing said portion of said sample for said preselected analyte in said detection zone.

4. An apparatus as described in claim 3, wherein said means for nebulizing at least a portion of such a sample comprises, means for injecting a portion of such a sample at a preselected rate into a nebulizing zone, and means for injecting an inert gas into said nebulizing zone at a preselected rate to form an aerosol with said portion of such a sample.

5. Apparatus for analyzing a sample, comprising:

a reduction tube with an inlet sleeve having a hydrogen inlet adjacent said inlet sleeve for supplying excess hydrogen to said tube, and having at the opposite end from said inlet sleeve a discharge end containing therein a gas discharge outlet, a nebulizer sealingly connected to said inlet sleeve so as to discharge into said reduction tube an aerosol of said sample and an inert gas, and a detector for analyzing gases from said reduction tube for a preselected analyte connected to said discharge outlet.

6. The apparatus of claim 5, further comprising, a supply of inert gas connected to said nebulizer, a supply of hydrogen connected to said hydrogen inlet of said reduction tube, and a pump connected to said nebulizer for supplying a portion of said sample to said nebulizer.

7. The apparatus of claim 6, further comprising, a filter interconnected between said outlet and said detector for filtering gases from said reduction tube.

8. Apparatus for decomposing a sample, comprising:

a reduction tube having an inlet end having a hydrogen inlet adjacent said inlet end for supplying excess hydrogen to said tube, and having at the opposite end from said inlet end a discharge end containing therein a gas discharge outlet, and a nebulizer operatively connected to said reduction tube so as to discharge into said reduction tube an aerosol of said sample and an inert gas.

9. A method for decomposing a sample, comprising:
nebulizing at least a portion of said sample,
transporting said nebulized sample to a decomposition zone, and
decomposing said sample in a hydrogen-rich atmosphere of hydrogen and an inert gas at a temperature sufficient to ensure complete reduction of said sample.

10. A method as described in claim 9, wherein said nebulizing comprises,
injecting a portion of said sample at a preselected rate into a nebulizing zone, and
injecting an inert gas into said nebulizing zone at a preselected rate to form an aerosol with said injected sample.

* * * * *